US007884091B2

(12) United States Patent
Belanoff

(10) Patent No.: US 7,884,091 B2
(45) Date of Patent: Feb. 8, 2011

(54) METHODS FOR TREATING DELIRIUM USING GLUCOCORTICOID RECEPTOR-SPECIFIC ANTAGONISTS

(75) Inventor: Joseph K. Belanoff, Woodside, CA (US)

(73) Assignee: Corcept Therapeutics, Inc. DE (US)

( * ) Notice: Subject to any disclaimer, the term of this patent is extended or adjusted under 35 U.S.C. 154(b) by 1071 days.

(21) Appl. No.: 11/383,017

(22) Filed: May 12, 2006

(65) Prior Publication Data

US 2006/0194713 A1    Aug. 31, 2006

Related U.S. Application Data

(63) Continuation of application No. 10/257,656, filed as application No. PCT/US02/14318 on May 6, 2002, now Pat. No. 7,163,934, which is a continuation-in-part of application No. 10/137,800, filed on May 1, 2002, now abandoned.

(60) Provisional application No. 60/288,619, filed on May 4, 2001.

(51) Int. Cl.
    *A61K 31/56*    (2006.01)
(52) U.S. Cl. .................. 514/171; 514/179; 514/180
(58) Field of Classification Search .............. 514/171, 514/179, 180
    See application file for complete search history.

(56) References Cited

U.S. PATENT DOCUMENTS 6,150,349 A    11/2000    Schatzberg et al.

FOREIGN PATENT DOCUMENTS

| WO | WO 99/17779 A1 | 4/1999 |
| WO | WO 99/59596 A1 | 11/1999 |
| WO | WO 02/076390 A2 | 10/2002 |

OTHER PUBLICATIONS

Berkow, R., et al., "Brain and Nerve Disorders: Delirium and Dementia" *The Merck Manual of Medical Information (Home Edition)*, 1997, pp. 396-398.
Campbell, K., et al., "Delirium After Cessation of Glucocorticoid Therapy," *General Hospital Psychiatry*, 1991, pp. 270-272, vol. 13, New York, U.S.A.
Fang, V.S. and J.B. Jaspan; "Delirium and neuromuscular symptoms in an elderly man with isolated corticotroph-deficiency syndrome completely reversed with glucocorticoid replacement"; *J. Clin. Endocrinol. Metab.*; 1989; pp. 1073-1077; vol. 69, No. 5.
O'Keeffe, S.T., et al., "Delirium and the Dexamethasone Suppression Test in the Elderly," *Neuropsychobiology*, 1994, pp. 153-156, vol. 30.

*Primary Examiner*—San-ming Hui
(74) *Attorney, Agent, or Firm*—Kilpatrick Townsend & Stockton LLP

(57) ABSTRACT

This invention generally pertains to the field of psychiatry. In particular, this invention pertains to the discovery that agents which inhibit the binding of cortisol to its receptors can be used in methods for treating delirium. Mifepristone, a potent specific glucocorticoid receptor antagonist, can be used in these methods. The invention also provides a kit for treating delirium in a human including a glucocorticoid receptor antagonist and instructional material teaching the indications, dosage and schedule of administration of the glucocorticoid receptor antagonist.

7 Claims, No Drawings

METHODS FOR TREATING DELIRIUM USING GLUCOCORTICOID RECEPTOR-SPECIFIC ANTAGONISTS

CROSS-REFERENCES TO RELATED APPLICATIONS

This application is a continuation application claiming priority to U.S. application Ser. No. 10/257,656, filed Oct. 15, 2002, which is a U.S. National Phase Application, filed under 35 U.S.C. §371 of Patent Cooperation Treaty Application Number PCT/US02/14318, filed May 6, 2002, which is a continuation-in-part of U.S. application Ser. No. 10/137,800, filed May 1, 2002 and claims priority to U.S. Provisional Application No. 60/288,619, filed May 4, 2001. Each of the aforementioned applications are hereby incorporated by reference in their entirety and for all purposes.

STATEMENT AS TO RIGHTS TO INVENTIONS MADE UNDER FEDERALLY SPONSORED RESEARCH AND DEVELOPMENT

Not Applicable

REFERENCE TO A "SEQUENCE LISTING," A TABLE, OR A COMPUTER PROGRAM LISTING APPENDIX SUBMITTED ON A COMPACT DISK

Not Applicable

FIELD OF THE INVENTION

This invention generally pertains to the field of psychiatry. In particular, this invention pertains to the discovery that agents that inhibit the binding of cortisol to the glucocorticoid receptor can be used in methods of treating delirium.

BACKGROUND OF THE INVENTION

Delirium is a disturbance in consciousness that typically results from an underlying physical condition. Patients suffering from delirium display changes in cognition (such as memory deficits, disorientation, and language or perceptual disturbances) that develop over a short period of time and tend to fluctuate during the course of the day.

The neurophysiological causes of delirium are not known in detail. The predominant neurochemical hypothesis for the origin of delirium focuses on underactivity of cholinergic neurotransmission in particular domains of the brain (see Trzepacz, *Dement Geriatr Cogn Disord* 10:330-334 (1999)). However, abnormalities in other neurotransmitters—such as serotonin, dopamine, gamma-aminobutryic acid, and glutamate—may also be involved in the development of delirium under particular conditions (see Flacker & Lipsitz, *J Gerontol A Biol Sci Med Sci* 54:B239-46 (1999)).

Cortisol, a glucocorticoid hormone secreted in response to ACTH (corticotropin), shows circadian rhythm variation, and further, is an important element in responsiveness to many physical and psychological stresses. It has been proposed that, with age, the cortisol regulatory system becomes hyperactivated in some individuals, resulting in hypercortisolemia. It has additionally been postulated that high levels of cortisol are neurotoxic, particularly in the hippocampus, a brain structure that is thought to be central to the processing and temporary storage of complex information and memory (see, e.g., Sapolsky et al., *Ann. NY Acad. Sci.* 746:294-304, 1994; Silva, *Annu. Rev. Genet.* 31:527-546, 1997; de Leon et al., *J. Clin. Endocrinol & Metab.* 82:3251, 1997).

The brain and CNS actions of cortisol and other glucocorticoids are not limited to neurotoxicity, however. In addition to influencing cerebral blood flow, oxygen consumption, and cerebral excitability, glucocorticoids have extensive effects on neurotransmitter function (see DeKloet et al., *Handbook Neurochem* 8:47-91 (1985)). These effects include inhibition of binding to central muscarinic cholinergic receptors, as well as modulation of serotonin turnover, hypothalamic dopamine balance, and suppression of beta-endorphin levels in the brain. The ability of glucocorticoids to perturb neurotransmitters involved in the pathogenesis of delirium suggests that disturbance of glucocorticoid regulation might play a role in delirium. However, while pathologically elevated glucocorticoid levels (due to adrenal dysfunction or ingestion of synthetic hormones) have been connected with the induction of delirium (see Stroudemire et al., *Gen Hosp Psychiatry* 18:196-202 (1996)), the relationship between physiological glucocorticoid levels and delirium remains unclear (for review see Flacker & Lipsitz, *J Gerontol A Biol Sci Med Sci* 54:B239-46 (1999)). Assessments of hypothalamic-pituitary-adrenal axis function in delirious patients by dexamethasone-suppression testing have been conflicting (see Koponen et al., *Nord Psykiatr Tidsskr* 43:203-207 (1987); McKeith, *Br J Psychiatry* 145:389-393 (1984); O'Keefe & Devline, *Neuropsychobiology* 30:153-156 (1994)). Furthermore, while some studies measuring glucocorticoid levels directly have found an association between delirium and persistent hypercortisolism (Gustafson et al., *Cerebrovasc Dis* 3:33-38 (1993)), other studies have failed to link the incidence of delirium with elevated cortisol levels (van der Mast et al., in Filippini ed., *Recent Advances in Tryptophan Research*, New York: Plenum Press, 93-96 (1996); McIntosh et al., *Psychoneuroendocrinology* 10:303-313 (1985)).

There has been no evidence prior to this invention, however, that a glucocorticoid receptor antagonist can be an effective treatment for delirium, especially in patients having cortisol levels that fall within a normal range. Many of the actions of cortisol are mediated by binding to the type I (mineralocorticoid) receptor, which is preferentially occupied, relative to the type II (glucocorticoid) receptor, at physiological cortisol levels. As cortisol levels increase, more glucocorticoid receptors are occupied and activated. Because cortisol plays an essential role in metabolism, inhibition of all cortisol-mediated activities, however, would be fatal. Therefore, antagonists that specifically prevent type II glucocorticoid receptor functions, but do not antagonize type I mineralocorticoid receptor functions are of particular use in this invention. Mifepristone (RU486) and similar antagonists are examples of this category of receptor antagonists.

The present inventors have determined that glucocorticoid receptor antagonists such as RU486 are effective agents for the specific treatment of delirium in patients with normal or decreased cortisol levels. The present invention therefore fulfills the need for an effective treatment for the symptoms of delirium by providing methods of administering glucocorticoid receptor antagonists to treat patients diagnosed with delirium.

BRIEF SUMMARY OF THE INVENTION

The invention provides a method of ameliorating the symptoms of delirium in a patient who has normal or decreased cortisol levels. The method comprises administration of a therapeutically effective amount of a glucocorticoid receptor antagonist to the patient.

In one embodiment of the invention, the method of treating delirium uses a glucocorticoid receptor antagonist comprising a steroidal skeleton with at least one phenyl-containing moiety in the 11-beta position of the steroidal skeleton. The phenyl-containing moiety in the 11-beta position of the steroidal skeleton can be a dimethylaminophenyl moiety. In alternative embodiments, the glucocorticoid receptor antagonist comprises mifepristone, or, the glucocorticoid receptor antagonist is selected from the group consisting of RU009 and RU044.

In other embodiments, the glucocorticoid receptor antagonist is administered in a daily amount of between about 0.5 to about 20 mg per kilogram of body weight per day; between about 1 to about 10 mg per kilogram of body weight per day; or between about 1 to about 4 mg per kilogram of body weight per day. The administration can be once per day. In alternative embodiments, the mode of glucocorticoid receptor antagonist administration is oral, or by a transdermal application, by a nebulized suspension, or by an aerosol spray.

The invention also provides a kit for the treatment of delirium in a human, the kit comprising a glucocorticoid receptor antagonist; and, an instructional material teaching the indications, dosage and schedule of administration of the glucocorticoid receptor antagonist. In alternative embodiments, the instructional material indicates that the glucocorticoid receptor antagonist can be administered in a daily amount of about 0.5 to about 20 mg per kilogram of body weight per day, of about 1 to about 10 mg per kilogram of body weight per day, or about 1 to about 4 mg per kilogram of body weight per day. The instructional material can indicate that cortisol contributes to delirium symptoms in patients with delirium, and that the glucocorticoid receptor antagonist can be used to treat delirium. In one embodiment, the glucocorticoid receptor antagonist in the kit is mifepristone. The mifepristone can in tablet form.

A further understanding of the nature and advantages of the present invention is realized by reference to the remaining portions of the specification and claims.

All publications, patents and patent applications cited herein are hereby expressly incorporated by reference for all purposes.

DEFINITIONS

The term "treating" refers to any indicia of success in the treatment or amelioration of an injury, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination, neuropsychiatric exams, and/or a psychiatric evaluation. For example, the methods of the invention successfully treat a patient's delirium by decreasing the incidence of disturbances in consciousness or cognition.

The term "delirium" refers to a psychiatric condition in its broadest sense, as defined in American Psychiatric Association: Diagnostic and Statistical Manual of Mental Disorders, Fourth Edition, Text Revision, Washington, D.C., 2000 ("DSM-IV-TR"). The DSM-IV-TR defines "delirium" as a disturbance of consciousness, developing over a short period of time, accompanied by a change in cognition that cannot be better accounted for by a preexisting or evolving dementia. The DSM-IV-TR sets forth a generally accepted standard for diagnosing and categorizing delirium.

The term "cortisol" refers to a family of compositions also referred to as hydrocortisone, and any synthetic or natural analogues thereof.

The term "glucocorticoid receptor" ("GR") refers to a family of intracellular receptors also referred to as the cortisol receptor, which specifically bind to cortisol and/or cortisol analogs. The term includes isoforms of GR, recombinant GR and mutated GR.

The term "mifepristone" refers to a family of compositions also referred to as RU486, or RU38.486, or 17-beta-hydroxy-11-beta-(4-dimethyl-aminophenyl)-17-alpha-(1-propynyl)-estra-4,9-dien-3-one), or 11-beta-(4dimethylaminophenyl)-17-beta-hydroxy-17-alpha-(1-propynyl)-estra-4,9-dien-3-one), or analogs thereof, which bind to the GR, typically with high affinity, and inhibit the biological effects initiated/mediated by the binding of any cortisol or cortisol analogue to a GR receptor. Chemical names for RU-486 vary; for example, RU486 has also been termed: 11B-[p-(Dimethylamino)phenyl]—
17B-hydroxy-17-(1-propynyl)-estra-4,9-dien-3-one; 11B-(4-dimethyl-aminophenyl)-
17B-hydroxy-17A-(prop-1-ynyl)-estra-4,9-dien-3-one;
17B-hydroxy-11B-(4-dimethylaminophenyl-1)-17A-(propynyl-1)-estra-4,9-diene-3-one; 17B-hydroxy-11B-(4-dimethylaminophenyl-1)-17A-(propynyl-1)-E; (11B, 17B)-11-[4-dimethylamino)-phenyl]-17-hydroxy-17-(1-propynyl)estra-4,9-dien-3-one; and 11B-[4-(N,N-dimethylamino)phenyl]-17A-(prop-1-ynyl)-D-4,9-estradiene-17B-ol-3-one.

The term "specific glucocorticoid receptor antagonist" refers to any composition or compound which partially or completely inhibits (antagonizes) the binding of a glucocorticoid receptor (GR) agonist, such as cortisol, or cortisol analogs, synthetic or natural, to a GR. A "specific glucocorticoid receptor antagonist" also refers to any composition or compound which inhibits any biological response associated with the binding of a GR to an agonist. By "specific", we intend the drug to preferentially bind to the GR rather than the mineralocorticoid receptor (MR) with an affinity at least 100-fold, and frequently 1000-fold.

A patient "not otherwise in need of treatment with a glucocorticoid receptor antagonist" is a patient who is not suffering from a condition which is known in the art to be effectively treatable with glucocorticoid receptor antagonists. Conditions known in the art to be effectively treatable with glucocorticoid receptor antagonists include Cushing's disease, drug withdrawal, psychosis, dementia, stress disorders, and psychotic major depression.

DETAILED DESCRIPTION

This invention pertains to the surprising discovery that agents that can inhibit glucocorticoid-induced biological responses are effective for treating delirium. In treating delirium, the methods of the invention can preferably relieve the symptoms of delirium or lead to complete resolution of the underlying disorder itself. In one embodiment, the methods of the invention use agents that act as GR antagonists, blocking the interaction of cortisol with GR, to treat or ameliorate delirium or symptoms associated with delirium. The methods of the invention are effective in ameliorating the symptoms of a delirium patient afflicted with either normal, increased or decreased levels of cortisol or other glucocorticoids, natural or synthetic.

Cortisol acts by binding to an intracellular, glucocorticoid receptor (GR). In humans, glucocorticoid receptors are present in two forms: a ligand-binding GR-alpha of 777 amino acids; and, a GR-beta isoform that differs in only the last fifteen amino acids. The two types of GR have high affinity for their specific ligands, and are considered to function through the same transduction pathways.

The biologic effects of cortisol, including pathologies or dysfunctions caused by hypercortisolemia, can be modulated and controlled at the GR level using receptor antagonists. Several different classes of agents are able to act as GR antagonists, i.e., to block the physiologic effects of GR-agonist binding (the natural agonist is cortisol). These antagonists include compositions, which, by binding to GR, block the ability of an agonist to effectively bind to and/or activate the GR. One family of known GR antagonists, mifepristone and related compounds, are effective and potent anti-glucocorticoid agents in humans (Bertagna, *J. Clin. Endocrinol. Metab.* 59:25, 1984). Mifepristone binds to the GR with high affinity, with a K of dissociation<$10^{-9}$M (Cadepond, *Annu. Rev. Med.* 48:129, 1997). Thus, in one embodiment of the invention, mifepristone and related compounds are used to treat delirium.

Delirium typically manifests itself with a variety of symptoms, including memory impairment, disorientation, perceptual disturbances, disturbances in the sleep-wake cycle, and disturbed psychomotor behavior. Thus, a variety of means of diagnosing delirium and assessing the success of treatment, i.e., the success and extent the symptoms of delirium are lessened by the methods of the invention, can be used, and a few exemplary means are set forth herein. These means can include classical, subjective psychological evaluations and neuropsychiatric examinations as described below.

As the methods of the invention include use of any means to inhibit the biological effects of an agonist-bound GR, illustrative compounds and compositions which can be used to treat delirium are also set forth. Routine procedures that can be used to identify further compounds and compositions able to block the biological response caused by a GR-agonist interaction for use in practicing the methods of the invention are also described. As the invention provides for administering these compounds and compositions as pharmaceuticals, routine means to determine GR antagonist drug regimens and formulations to practice the methods of the invention are set forth below.

1. Diagnosis of Delirium

Delirium is characterized by disturbances of consciousness and changes in cognition that develop over a relatively short period of time. The disturbance in consciousness is often manifested by a reduced clarity of awareness of the environment. The patient displays reduced ability to focus, sustain or shift attention (DSM-IV-TR diagnostic Criterion A). Accompanying the disturbance in consciousness, delirium patients display a disturbance in cognition (e.g., memory impairment, disorientation, language difficulties) or perceptual disturbances (e.g., misinterpretations, illusions, or hallucinations) (Criterion B). To be considered delirium, these disturbances in consciousness, cognition, or perception should develop over a short period of time and tend to fluctuate during the course of the day (Criterion C).

The glucocorticoid receptor antagonists of the present invention are effective in treating delirium arising from any of several possible etiologies. Delirium may arise from a number of general medical conditions, including central nervous system disorders (e.g., trauma, stroke, encephalopathies), metabolic disorders (e.g., renal or hepatic insufficiency, fluid or electrolyte imbalances), cardiopulmonary disorders (e.g., congestive heart failure, myocardial infarction, shock), and systemic illnesses or effects (e.g., infections, sensory deprivation, and postoperative states). Glucocorticoid receptor antagonists are also effective to treat Substance-Induced Delirium (e.g., delirium induced by substance intoxication or withdrawal, medication side effects, and toxin exposure). Delirium may arise from multiple simultaneous etiologies (e.g., a combination of a general medical condition and substance intoxication) and such delirium, as well as delirium of unknown or unclassified origin, may be treated with the glucocorticoid receptor antagonists of the present invention.

A diagnosis of delirium is distinct from a diagnosis of dementia or psychosis. Although memory impairment is common in both delirium and dementia, a patient with dementia alone is alert and usually does not display the disturbance in consciousness that is characteristic of delirium. Dementia patients typically lack the waxing and waning of symptoms over a 24-hour period that characterizes delirium. Likewise, while delusions, hallucinations and agitation may be a feature of both delirium and psychosis, psychotic patients suffer from a basic disturbance in thought content. In contrast, delirious patients primarily suffer from disturbances in perception and orientation, rather than internal thought content. Psychotic symptoms, if present, tend to be fragmented rather than systematic. Delirium is also distinguished from dementia, psychosis, stress disorders, and mood disorders by the characteristic waxing and waning of symptoms, by signature EEG abnormalities described herein, and by the presence of a precipitating factor such as a general medical condition or substance intoxication.

Delirium may be diagnosed and evaluated with any one of several objective, standardized test instruments known in the art, although skilled clinicians may readily diagnose delirium through unstructured clinical interactions. Standardized test instruments are constructed by experienced clinical researchers based on DSM diagnostic criteria, and are typically validated through statistical studies and comparisons of various patient populations. Generally, standardized instruments assess both manifest psychological or physiological symptoms as well as internal thought processes. The presence and severity of delirium may be determined by assessing disturbances in arousal, level of consciousness, cognitive function (e.g., memory, attention, orientation, disturbances in thinking) and psychomotor activity. Standardized test instruments for the diagnosis of delirium are usually administered by a professional health care practitioner, and may comprise interactive examination as well as observation of patient behavior.

Standardized test instruments for assessing delirium include the Delirium Rating Scale (for review see Trzepacz, *Psychosomatics* 40:193-204 (1999)), the Memorial Delirium Assessment Scale (Breitbart et al., *J Pain Symptom Manage* 13:128-137 (1997)), the Delirium Severity Scale (Bettin et al., *Am J Geriatr Psychiatry* 6:296-307 (1998)), and the Delirium Symptom Interview (Albert et al., *J Geriatr Psychiatry Neurol* 5:14-21 (1992)). Cutoff scores yielding the most statistically valid division of patients into delirium and non-delirium populations are calculated based on optimal positive and negative predictive power, and have been established and reported for each test (e.g., a score of 13 or greater on the Memorial Delirium Assessment Scale or a score of 10 or greater on the Delirium Rating Scale) and may be used to select patients for therapy.

Delirium may also be diagnosed and rated by the use of electroencephalography (EEG) (for review see Jacobson & Jerrier, *Semin Clin Neuropsychiatry*, 5:86-92 (2000)). Electroencephalograms of delirium patients are marked by a characteristic slowing or dropout of the posterior dominant rhythm, generalized theta or delta slow-wave activity, poor organization of the background rhythm, and loss of reactivity of the EEG to eye opening and closing. Delirium patients may also be diagnosed by quantitative EEG (QEEG), in which they display increased absolute and relative slow-wave (theta and delta) power, reduced ratio of fast-to-slow band power, reduced mean frequency, and reduced occipital peak frequency. Accordingly, EEG or QEEG may be used to select patients for treatment with glucocorticoid receptor antagonists, or to monitor the effectiveness of glucocorticoid receptor antagonist therapy.

2. General Laboratory Procedures

When practicing the methods of the invention, a number of general laboratory tests can be used to assist in the diagnosis, progress and prognosis of the patient with delirium, including monitoring of parameters such as blood cortisol, drug metabolism, brain structure and function and the like. These procedures can be helpful because all patients metabolize and react to drugs uniquely. In addition, such monitoring may be important because each GR antagonist has different pharmacokinetics. Different patients and disease conditions may require different dosage regimens and formulations. Such procedures and means to determine dosage regimens and formulations are well described in the scientific and patent literature. A few illustrative examples are set forth below.

a. Determining Blood Cortisol Levels

Varying levels of blood cortisol have been associated with delirium, although the invention may also be practiced upon patients with apparently normal levels of blood cortisol. Thus, monitoring blood cortisol and determining baseline cortisol levels are useful laboratory tests to aid in the diagnosis, treatment and prognosis of a delirium patient. A wide variety of laboratory tests exist that can be used to determine whether an individual is normal, hypo- or hypercortisolemic. Delirium patients typically have normal levels of cortisol that are often less than 25 µg/dl in the morning, and frequently about 15 µg/dl or less in the afternoon, although the values often fall at the high end of the normal range, which is generally considered to be 5-15 µg/dl in the afternoon.

Immunoassays such as radioimmunoassays are commonly used because they are accurate, easy to do and relatively cheap. Because levels of circulating cortisol are an indicator of adrenocortical function, a variety of stimulation and suppression tests, such as ACTH Stimulation, ACTH Reserve, or dexamethasone suppression (see, e.g., Greenwald, *Am. J. Psychiatry* 143:442-446, 1986), can also provide diagnostic, prognostic or other information to be used adjunctively in the methods of the invention.

One such assay available in kit form is the radioimmunoassay available as "Double Antibody Cortisol Kit" (Diagnostic Products Corporation, Los Angeles, Calif.), (*Acta Psychiatr. Scand.* 70:239-247, 1984). This test is a competitive radioimmunoassay in which $^{125}$I-labeled cortisol competes with cortisol from an clinical sample for antibody sites. In this test, due to the specificity of the antibody and lack of any significant protein effect, serum and plasma samples require neither preextraction nor predilution. This assay is described in further detail in Example 2, below.

b. Determination of Blood/Urine Mifepristone Levels

Because a patient's metabolism, clearance rate, toxicity levels, etc. differs with variations in underlying primary or secondary disease conditions, drug history, age, general medical condition and the like, it may be necessary to measure blood and urine levels of GR antagonist. Means for such monitoring are well described in the scientific and patent literature. As in one embodiment of the invention mifepristone is administered to treat delirium, an illustrative example of determining blood and urine mifepristone levels is set forth in the Example below.

c. Other Laboratory Procedures

Because the presentation of delirium may be complex, a number of additional laboratory tests can be used adjunctively in the methods of the invention to assist in diagnosis, treatment efficacy, prognosis, toxicity and the like. For example, as increased hypercortisolemia has also been associated with delirium, diagnosis and treatment assessment can be augmented by monitoring and measuring glucocorticoid-sensitive variables, including but limited to fasting blood sugar, blood sugar after oral glucose administration, plasma concentrations thyroid stimulating hormone (TSH), corticosteroid-binding globulin, luteinizing hormone (LH), testosterone-estradiol-binding globulin, and/or total and free testosterone.

Laboratory tests monitoring and measuring GR antagonist metabolite generation, plasma concentrations and clearance rates, including urine concentration of antagonist and metabolites, may also be useful in practicing the methods of the invention. For example, mifepristone has two hydrophilic, N-monomethylated and N-dimethylated, metabolites. Plasma and urine concentrations of these metabolites (in addition to RU486) can be determined using, for example, thin layer chromatography, as described in Kawai *Pharmacol. and Experimental Therapeutics* 241:401-406, 1987.

3. Glucocorticoid Receptor Antagonists to Treat Delirium

The invention provides for methods of treating delirium utilizing any composition or compound that can block a biological response associated with the binding of cortisol or a cortisol analogue to a GR. Antagonists of GR activity utilized in the methods of the invention are well described in the scientific and patent literature. A few illustrative examples are set forth below.

a. Steroidal Anti-Glucocorticoids as GR Antagonists.

Steroidal glucocorticoid antagonists are administered for the treatment of delirium in various embodiments of the invention. Steroidal antiglucocorticoids can be obtained by modification of the basic structure of glucocorticoid agonists, i.e., varied forms of the steroid backbone. The structure of cortisol can be modified in a variety of ways. The two most commonly known classes of structural modifications of the cortisol steroid backbone to create glucocorticoid antagonists include modifications of the 11-beta hydroxy group and modification of the 17-beta side chain (see, e.g., Lefebvre, *J. Steroid Biochem.* 33:557-563, 1989).

i) Removal or Substitution of the 11-beta Hydroxy Group

Glucocorticoid agonists with modified steroidal backbones comprising removal or substitution of the 11-beta hydroxy group are administered in one embodiment of the invention. This class includes natural antiglucocorticoids, including cortexolone, progesterone and testosterone derivatives, and synthetic compositions, such as mifepristone (Lefebvre, et al. supra). Preferred embodiments of the invention include all 11-beta-aryl steroid backbone derivatives because these compounds are devoid of progesterone receptor (PR) binding activity (Agarwal, *FEBS* 217:221-226, 1987). Another preferred embodiment comprises an 11-beta phenyl-aminodimethyl steroid backbone derivative, i.e., mifepristone, which is both an effective anti-glucocorticoid and anti-progesterone agent. These compositions act as reversibly-binding steroid receptor antagonists. For example, when bound to a 11-beta phenyl-aminodimethyl steroid, the steroid receptor is maintained in a conformation that cannot bind its natural ligand, such as cortisol in the case of GR (Cadepond, 1997, supra).

Synthetic 11-beta phenyl-aminodimethyl steroids include mifepristone, also known as RU486, or 17-beta-hydrox-11-beta-(4-dimethyl-aminophenyl)17-alpha-(1-propynyl)estra-4,9-dien-3-one). Mifepristone has been shown to be a powerful antagonist of both the progesterone and glucocorticoid (GR) receptors. Another 11-beta phenyl-aminodimethyl steroids shown to have GR antagonist effects includes RU009 (RU39.009), 11-beta-(4-dimethyl-aminoethoxyphenyl)-17-alpha-(propynyl-17 beta-hydroxy-4,9-estradien-3-one) (see Bocquel, *J. Steroid Biochem. Molec. Biol.* 45:205-215, 1993). Another GR antagonist related to RU486 is RU044 (RU43.044) 17-beta-hydrox-17-alpha-19-(4-methyl-phenyl)-androsta-4,9 (11)-dien-3-one) (Bocquel, 1993, supra). See also Teutsch, *Steroids* 38:651-665, 1981; U.S. Pat. Nos. 4,386,085 and 4,912,097.

One embodiment includes compositions containing the basic glucocorticoid steroid structure which are irreversible anti-glucocorticoids. Such compounds include alpha-keto-methanesulfonate derivatives of cortisol, including cortisol-21-mesylate (4-pregnene-11-beta, 17-alpha, 21-triol-3, 20-dione-21-methane-sulfonate and dexamethasone-21-mesylate (16-methyl-9 alpha-fluoro-1,4-pregnadiene-11 beta, 17-alpha, 21-triol-3, 20-dione-21-methane-sulfonate). See Simons, *J. Steroid Biochem.* 24:25-32 1986; Mercier, *J. Steroid Biochem.* 25:11-20, 1986; U.S. Pat. No. 4,296,206.

ii) Modification of the 17-beta Side Chain Group

Steroidal antiglucocorticoids which can be obtained by various structural modifications of the 17-beta side chain are also used in the methods of the invention. This class includes synthetic antiglucocorticoids such as dexamethasone-oxetanone, various 17, 21-acetonide derivatives and 17-beta-carboxamide derivatives of dexamethasone (Lefebvre, 1989, supra; Rousseau, *Nature* 279:158-160, 1979).

iii) Other Steroid Backbone Modifications

GR antagonists used in the various embodiments of the invention include any steroid backbone modification which effects a biological response resulting from a GR-agonist interaction. Steroid backbone antagonists can be any natural or synthetic variation of cortisol, such as adrenal steroids missing the C-19 methyl group, such as 19-nordeoxycorticosterone and 19-norprogesterone (Wynne, *Endocrinology* 107:1278-1280, 1980).

In general, the 11-beta side chain substituent, and particularly the size of that substituent, can play a key role in determining the extent of a steroid's antiglucocorticoid activity. Substitutions in the A ring of the steroid backbone can also be important. 17-hydroxypropenyl side chains generally decrease antiglucocorticoid activity in comparison to 17-propinyl side chain containing compounds.

Additional glucocorticoid receptor antagonists known in the art and suitable for practice of the invention include 21-hydroxy-6,19-oxidoprogesterone (see Vicent, *Mol. Pharm.* 52:749-753 (1997)), Org31710 (see Mizutani, *J Steroid Biochem Mol Biol* 42(7):695-704 (1992)), Org34517, RU43044, RU40555 (see Kim, *J Steroid Biochem Mol Biol.* 67(3):213-22 (1998)), RU28362, and ZK98299.

b. Non-Steroidal Anti-Glucocorticoids as Antagonists.

Non-steroidal glucocorticoid antagonists are also used in the methods of the invention to treat delirium. These include synthetic mimetics and analogs of proteins, including partially peptidic, pseudopeptidic and non-peptidic molecular entities. For example, oligomeric peptidomimetics useful in the invention include (alpha-beta-unsaturated) peptidosulfonamides, N-substituted glycine derivatives, oligo carbamates, oligo urea peptidomimetics, hydrazinopeptides, oligosulfones and the like (see, e.g., Amour, *Int. J. Pept. Protein Res.* 43:297-304, 1994; de Bont, *Bioorganic & Medicinal Chem.* 4:667-672, 1996). The creation and simultaneous screening of large libraries of synthetic molecules can be carried out using well-known techniques in combinatorial chemistry, for example, see van Breemen, *Anal Chem* 69:2159-2164, 1997; and Lam, *Anticancer Drug Des* 12:145-167, 1997. Design of peptidomimetics specific for GR can be designed using computer programs in conjunction with combinatorial chemistry (combinatorial library) screening approaches (Murray, *J. of Computer-Aided Molec. Design* 9:381-395, 1995; Bohm, *J. of Computer-Aided Molec. Design* 10:265-272, 1996). Such "rational drug design" can help develop peptide isomerics and conformers including cycloisomers, retro-inverso isomers, retro isomers and the like (as discussed in Chorev, *TibTech* 13:438-445, 1995).

c. Identifying Specific Glucocorticoid Receptor Antagonists

Because any specific GR antagonist can be used for the treatment of delirium in the methods of the invention, in addition to the compounds and compositions described above, additional useful GR antagonists can be determined by the skilled artisan. A variety of such routine, well-known methods can be used and are described in the scientific and patent literature. They include in vitro and in vivo assays for the identification of additional GR antagonists. A few illustrative examples are described below.

One assay that can be used to identify a GR antagonist of the invention measures the effect of a putative GR antagonist on tyrosine amino-transferase activity in accordance with the method of Granner, *Meth. Enzymol.* 15:633, 1970. This analysis is based on measurement of the activity of the liver enzyme tyrosine amino-transferase (TAT) in cultures of rat hepatoma cells (RHC). TAT catalyzes the first step in the metabolism of tyrosine and is induced by glucocorticoids (cortisol) both in liver and hepatoma cells. This activity is easily measured in cell extracts. TAT converts the amino group of tyrosine to 2-oxoglutaric acid. P-hydroxyphenylpyruvate is also formed. It can be converted to the more stable p-hydroxybenzaldehyde in an alkaline solution and quantitated by absorbance at 331 nm. The putative GR antagonist is co-administered with cortisol to whole liver, in vivo or ex vivo, or hepatoma cells or cell extracts. A compound is identified as a GR antagonist when its administration decreases the amount of induced TAT activity, as compared to control (i.e., only cortisol or GR agonist added) (see also Shirwany, *Biochem. Biophys. Acta* 886:162-168, 1986).

Further illustrative of the many assays which can be used to identify compositions utilized in the methods of the invention, in addition to the TAT assay, are assays based on glucocorticoid activities in vivo. For example, assays that assess the ability of a putative GR antagonist to inhibit uptake of $^3$H-thymidine into DNA in cells which are stimulated by glucocorticoids can be used. Alternatively, the putative GR antagonist can complete with $^3$H-dexamethasone for binding to a hepatoma tissue culture GR (see, e.g., Choi, et al., *Steroids* 57:313-318, 1992). As another example, the ability of a putative GR antagonist to block nuclear binding of $^3$H-dexamethasone-GR complex can be used (Alexandrova et al., *J. Steroid Biochem. Mol. Biol.* 41:723-725, 1992). To further identify putative GR antagonists, kinetic assays able to discriminate between glucocorticoid agonists and antagonists by means of receptor-binding kinetics can also be used (as described in Jones, *Biochem J.* 204:721-729, 1982).

In another illustrative example, the assay described by Daune, *Molec. Pharm.* 13:948-955, 1977; and in U.S. Pat.

No. 4,386,085, can be used to identify anti-glucocorticoid activity. Briefly, the thymocytes of adrenalectomized rats are incubated in nutritive medium containing dexamethasone with the test compound (the putative GR antagonist) at varying concentrations. $^3$H-uridine is added to the cell culture, which is further incubated, and the extent of incorporation of radiolabel into polynucleotide is measured. Glucocorticoid agonists decrease the amount of $^3$H-uridine incorporated. Thus, a GR antagonist will oppose this effect.

For additional compounds that can be utilized in the methods of the invention and methods of identifying and making such compounds, see U.S. Pat. No. 4,296,206 (see above); U.S. Pat. No. 4,386,085 (see above); U.S. Pat. Nos. 4,447,424; 4,477,445; 4,519,946; 4,540,686; 4,547,493; 4,634,695; 4,634,696; 4,753,932; 4,774,236; 4,808,710; 4,814,327; 4,829,060; 4,861,763; 4,912,097; 4,921,638; 4,943,566; 4,954,490; 4,978,657; 5,006,518; 5,043,332; 5,064,822; 5,073,548; 5,089,488; 5,089,635; 5,093,507; 5,095,010; 5,095,129; 5,132,299; 5,166,146; 5,166,199; 5,173,405; 5,276,023; 5,380,839; 5,348,729; 5,426,102; 5,439,913; and 5,616,458; and WO 96/19458, which describes non-steroidal compounds which are high-affinity, highly selective modulators (antagonists) for steroid receptors, such as 6-substituted-1,2-dihydro N-1 protected quinolines.

The specificity of the antagonist for the GR relative to the MR can be measured using a variety of assays known to those of skill in the art. For example, specific antagonists can be identified by measuring the ability of the antagonist to bind to the GR compared to the MR (see, e.g., U.S. Pat. Nos. 5,606,021; 5,696,127; 5,215,916; 5,071,773). Such an analysis can be performed using either direct binding assay or by assessing competitive binding to the purified GR or MR in the presence of a known antagonist. In an exemplary assay, cells that are stably expressing the glucocorticoid receptor or mineralocorticoid receptor (see, e.g., U.S. Pat. No. 5,606,021) at high levels are used as a source of purified receptor. The affinity of the antagonist for the receptor is then directly measured. Those antagonists that exhibit at least a 100-fold higher affinity, often 1000-fold, for the GR relative to the MR are then selected for use in the methods of the invention.

A GR-specific antagonist may also be defined as a compound that has the ability to inhibit GR-mediated activities, but not MR-mediated activities. One method of identifying such a GR-specific antagonist is to assess the ability of an antagonist to prevent activation of reporter constructs using transfection assays (see, e.g., Bocquel et al, *J. Steroid Biochem Molec. Biol.* 45:205-215, 1993, U.S. Pat. Nos. 5,606,021, 5,929,058). In an exemplary transfection assay, an expression plasmid encoding the receptor and a reporter plasmid containing a reporter gene linked to receptor-specific regulatory elements are cotransfected into suitable receptor-negative host cells. The transfected host cells are then cultured in the presence and absence of a hormone, such as cortisol or analog thereof, able to activate the hormone responsive promoter/enhancer element of the reporter plasmid. Next the transfected and cultured host cells are monitored for induction (i.e., the presence) of the product of the reporter gene sequence. Finally, the expression and/or steroid binding-capacity of the hormone receptor protein (coded for by the receptor DNA sequence on the expression plasmid and produced in the transfected and cultured host cells), is measured by determining the activity of the reporter gene in the presence and absence of an antagonist. The antagonist activity of a compound may be determined in comparison to known antagonists of the GR and MR receptors (see, e.g., U.S. Pat. No. 5,696,127). Efficacy is then reported as the percent maximal response observed for each compound relative to a reference antagonist compound. A GR-specific antagonist is considered to exhibit at least a 100-fold, often 1000-fold or greater, activity towards the GR relative to the MR.

4. Treatment of Delirium Using Glucocorticold Receptor Antagonists

Antiglucocorticoids, such as mifepristone, are formulated as pharmaceuticals to be used in the methods of the invention to treat delirium. Any composition or compound that can block a biological response associated with the binding of cortisol or a cortisol analogue to a GR can be used as a pharmaceutical in the invention. Routine means to determine GR antagonist drug regimens and formulations to practice the methods of the invention are well described in the patent and scientific literature, and some illustrative examples are set forth below.

a. Glucocorticoid Receptor Antagonists as Pharmaceutical Compositions

The GR antagonists used in the methods of the invention can be administered by any means known in the art, e.g., parenterally, topically, orally, or by local administration, such as by aerosol or transdermally. The methods of the invention provide for prophylactic and/or therapeutic treatments. The GR antagonists as pharmaceutical formulations can be administered in a variety of unit dosage forms depending upon the condition or disease and the degree of delirium, the general medical condition of each patient, the resulting preferred method of administration and the like. Details on techniques for formulation and administration are well described in the scientific and patent literature, see, e.g., the latest edition of Remington's Pharmaceutical Sciences, Maack Publishing Co, Easton Pa. ("Remington's").

GR antagonist pharmaceutical formulations can be prepared according to any method known to the art for the manufacture of pharmaceuticals. Such drugs can contain sweetening agents, flavoring agents, coloring agents and preserving agents. Any GR antagonist formulation can be admixtured with nontoxic pharmaceutically acceptable excipients which are suitable for manufacture.

Pharmaceutical formulations for oral administration can be formulated using pharmaceutically acceptable carriers well known in the art in appropriate and suitable dosages. Such carriers enable the pharmaceutical formulations to be formulated in unit dosage forms as tablets, pills, powder, dragees, capsules, liquids, lozenges, gels, syrups, slurries, suspensions, etc., suitable for ingestion by the patient. Pharmaceutical preparations for oral use can be obtained through combination of GR antagonist compounds with a solid excipient, optionally grinding a resulting mixture, and processing the mixture of granules, after adding suitable additional compounds, if desired, to obtain tablets or dragee cores. Suitable solid excipients are carbohydrate or protein fillers include, but are not limited to sugars, including lactose, sucrose, mannitol, or sorbitol; starch from corn, wheat, rice, potato, or other plants; cellulose such as methyl cellulose, hydroxypropylmethyl-cellulose, or sodium carboxymethylcellulose; and gums including arabic and tragacanth; as well as proteins such as gelatin and collagen. If desired, disintegrating or solubilizing agents may be added, such as the cross-linked polyvinyl pyrrolidone, agar, alginic acid, or a salt thereof, such as sodium alginate.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound (i.e., dosage). Pharmaceutical preparations of the invention can also be used orally using, for example, push-fit capsules made of gelatin, as well as soft, sealed capsules made of gelatin and a coating such as glycerol or sorbitol. Push-fit capsules can contain GR antagonist mixed with a filler or binders such as lactose or starches, lubricants such as talc or magnesium stearate, and, optionally, stabilizers. In soft capsules, the GR antagonist compounds may be dissolved or suspended in suitable liquids, such as fatty oils, liquid paraffin, or liquid polyethylene glycol with or without stabilizers.

Aqueous suspensions of the invention contain a GR antagonist in admixture with excipients suitable for the manufacture of aqueous suspensions. Such excipients include a suspending agent, such as sodium carboxymethylcellulose, methylcellulose, hydroxypropylmethylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethylene oxycetanol), a condensation product of ethylene oxide with a partial ester derived from a fatty acid and a hexitol (e.g., polyoxyethylene sorbitol mono-oleate), or a condensation product of ethylene oxide with a partial ester derived from fatty acid and a hexitol anhydride (e.g., polyoxyethylene sorbitan mono-oleate). The aqueous suspension can also contain one or more preservatives such as ethyl or n-propyl p-hydroxybenzoate, one or more coloring agents, one or more flavoring agents and one or more sweetening agents, such as sucrose, aspartame or saccharin. Formulations can be adjusted for osmolarity.

Oil suspensions can be formulated by suspending a GR antagonist in a vegetable oil, such as arachis oil, olive oil, sesame oil or coconut oil, or in a mineral oil such as liquid paraffin; or a mixture of these. The oil suspensions can contain a thickening agent, such as beeswax, hard paraffin or cetyl alcohol. Sweetening agents can be added to provide a palatable oral preparation, such as glycerol, sorbitol or sucrose. These formulations can be preserved by the addition of an antioxidant such as ascorbic acid. As an example of an injectable oil vehicle, see Minto, *J. Pharmacol. Exp. Ther.* 281:93-102, 1997. The pharmaceutical formulations of the invention can also be in the form of oil-in-water emulsions. The oily phase can be a vegetable oil or a mineral oil, described above, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsion can also contain sweetening agents and flavoring agents, as in the formulation of syrups and elixirs. Such formulations can also contain a demulcent, a preservative, or a coloring agent.

Dispersible powders and granules of the invention suitable for preparation of an aqueous suspension by the addition of water can be formulated from a GR antagonist in admixture with a dispersing, suspending and/or wetting agent, and one or more preservatives. Suitable dispersing or wetting agents and suspending agents are exemplified by those disclosed above. Additional excipients, for example, sweetening, flavoring and coloring agents, can also be present.

The GR antagonists of this invention can also be administered in the form of suppositories for rectal administration of the drug. These formulations can be prepared by mixing the drug with a suitable non-irritating excipient which is solid at ordinary temperatures but liquid at the rectal temperatures and will therefore melt in the rectum to release the drug. Such materials are cocoa butter and polyethylene glycols.

The GR antagonists of this invention can also be administered by in intranasal, intraocular, intravaginal, and intrarectal routes including suppositories, insufflation, powders and aerosol formulations (for examples of steroid inhalants, see Rohatagi, *J. Clin. Pharmacol.* 35:1187-1193, 1995; Tjwa, *Ann. Allergy Asthma Immunol.* 75:107-111, 1995).

The GR antagonists of the invention can be delivered by transdermally, by a topical route, formulated as applicator sticks, solutions, suspensions, emulsions, gels, creams, ointments, pastes, jellies, paints, powders, and aerosols.

The GR antagonists of the invention can also be delivered as microspheres for slow release in the body. For example, microspheres can be administered via intradermal injection of drug (e.g., mifepristone)-containing microspheres, which slowly release subcutaneously (see Rao, *J. Biomater Sci. Polym. Ed.* 7:623-645, 1995; as biodegradable and injectable gel formulations (see, e.g., Gao *Pharm. Res.* 12:857-863, 1995); or, as microspheres for oral administration (see, e.g., Eyles, *J. Pharm. Pharmacol.* 49:669-674, 1997). Both transdermal and intradermal routes afford constant delivery for weeks or months.

The GR antagonist pharmaceutical formulations of the invention can be provided as a salt and can be formed with many acids, including but not limited to hydrochloric, sulfuric, acetic, lactic, tartaric, malic, succinic, etc. Salts tend to be more soluble in aqueous or other protonic solvents that are the corresponding free base forms. In other cases, the preferred preparation may be a lyophilized powder in 1 mM-50 mM histidine, 0.1%-2% sucrose, 2%-7% mannitol at a pH range of 4.5 to 5.5, that is combined with buffer prior to use In another embodiment, the GR antagonist formulations of the invention are useful for parenteral administration, such as intravenous (IV) administration or administration into a body cavity or lumen of an organ. The formulations for administration will commonly comprise a solution of the GR antagonist (e.g., mifepristone) dissolved in a pharmaceutically acceptable carrier. Among the acceptable vehicles and solvents that can be employed are water and Ringer's solution, an isotonic sodium chloride. In addition, sterile fixed oils can conventionally be employed as a solvent or suspending medium. For this purpose any bland fixed oil can be employed including synthetic mono- or diglycerides. In addition, fatty acids such as oleic acid can likewise be used in the preparation of injectables. These solutions are sterile and generally free of undesirable matter. These formulations may be sterilized by conventional, well known sterilization techniques. The formulations may contain pharmaceutically acceptable auxiliary substances as required to approximate physiological conditions such as pH adjusting and buffering agents, toxicity adjusting agents, e.g., sodium acetate, sodium chloride, potassium chloride, calcium chloride, sodium lactate and the like. The concentration of GR antagonist in these formulations can vary widely, and will be selected primarily based on fluid volumes, viscosities, body weight, and the like, in accordance with the particular mode of administration selected and the patient's needs. For IV administration, the formulation can be a sterile injectable preparation, such as a sterile injectable aqueous or oleaginous suspension. This suspension can be formulated according to the known art using those suitable dispersing or wetting agents and suspending agents. The sterile injectable preparation can also be a sterile injectable solution or suspension in a nontoxic parenterally-acceptable diluent or solvent, such as a solution of 1,3-butanediol.

In another embodiment, the GR antagonist formulations of the invention can be delivered by the use of liposomes which fuse with the cellular membrane or are endocytosed, i.e., by employing ligands attached to the liposome, or attached directly to the oligonucleotide, that bind to surface membrane protein receptors of the cell resulting in endocytosis. By using liposomes, particularly where the liposome surface carries ligands specific for target cells, or are otherwise preferentially directed to a specific organ, one can focus the delivery of the GR antagonist into the target cells in vivo. (See, e.g., Al-Muhammed, *J. Microencapsul.* 13:293-306, 1996; Chonn, *Curr. Opin. Biotechnol.* 6:698-708, 1995; Ostro, *Am. J. Hosp. Pharm.* 46:1576-1587, 1989).

b. Determining Dosing Regimens for Glucocorticoid Receptor Antagonists

The methods of the invention treat delirium, i.e., reduce the incidence and severity of cognitive, perceptual, or consciousness disturbances. The amount of GR antagonist adequate to accomplish this is defined as a "therapeutically effective dose". The dosage schedule and amounts effective for this use, i.e., the "dosing regimen," will depend upon a variety of factors, including the stage of the disease or condition, the severity of the disease or condition, the general state of the patient's health, the patient's physical status, age and the like. In calculating the dosage regimen for a patient, the mode of administration also is taken into consideration.

The dosage regimen also takes into consideration pharmacokinetics parameters well known in the art, i.e., the GR antagonists' rate of absorption, bioavailability, metabolism, clearance, and the like (see, e.g., Hidalgo-Aragones (1996) *J. Steroid Biochem. Mol. Biol.* 58:611-617; Groning (1996) *Pharmazie* 51:337-341; Fotherby (1996) *Contraception* 54:59-69; Johnson (1995) *J. Pharm. Sci.* 84:1144-1146; Rohatagi (1995) *Pharmazie* 50:610-613; Brophy (1983) *Eur. J. Clin. Pharmacol.* 24:103-108; the latest Remington's, supra). For example, in one study, less than 0.5% of the daily dose of mifepristone was excreted in the urine; the drug bound extensively to circulating albumin (see Kawai (1989) supra). The state of the art allows the clinician to determine the dosage regimen for each individual patient, GR antagonist and disease or condition treated. As an illustrative example, the guidelines provided below for mifepristone can be used as guidance to determine the dosage regiment, i.e., dose schedule and dosage levels, of any GR antagonist administered when practicing the methods of the invention.

Single or multiple administrations of GR antagonist formulations can be administered depending on the dosage and frequency as required and tolerated by the patient. The formulations should provide a sufficient quantity of active agent, i.e., mifepristone, to effectively treat the delirium. Thus, one typical pharmaceutical formulations for oral administration of mifepristone is in a daily amount of between about 0.5 to about 20 mg per kilogram of body weight per day. In an alternative embodiment, dosages are from about 1 mg to about 4 mg per kg of body weight per patient per day are used. Lower dosages can be used, particularly when the drug is administered to an anatomically secluded site, such as the cerebral spinal fluid (CSF) space, in contrast to administration orally, into the blood stream, into a body cavity or into a lumen of an organ. Substantially higher dosages can be used in topical administration. Actual methods for preparing parenterally administrable GR antagonist formulations will be known or apparent to those skilled in the art and are described in more detail in such publications as Remington's, supra. See also Nieman, In "Receptor Mediated Antisteroid Action," Agarwal, et al., eds., De Gruyter, N.Y. (1987).

The duration of administration would be 5-14 days. After a pharmaceutical comprising a GR antagonist of the invention has been formulated in a acceptable carrier, it can be placed in an appropriate container and labeled for treatment of an indicated condition. For administration of GR antagonists, such labeling would include, e.g., instructions concerning the amount, frequency and method of administration. In one embodiment, the invention provides for a kit for the treatment of delirium in a human which includes a GR antagonist and instructional material teaching the indications, dosage and schedule of administration of the GR antagonist.

EXAMPLES

The following examples are offered to illustrate, but not to limit the claimed invention.

Example 1

Treating Delirium With Miferpistone

The following example demonstrates how to practice the methods of the invention.

Patient Selection

Individuals are diagnosed with delirium using subjective and objective criteria, including criteria as set forth by the DSM-IV-TR, as described above. The delirium patient typically has normal levels of cortisol for his or her age.

Dosage Regimen and Administration of Mifepristone

The glucocorticoid receptor (GR) antagonist, mifepristone, is used in this study. It is administered in dosages of 600-1200 mg daily for one week. Patients are evaluated as described below. Dosages will be adjusted if necessary and further evaluations will be performed periodically throughout treatment.

Mifepristone tablets are available from Shanghai HuaLian Pharmaceuticals Co., Ltd., Shanghai, China.

Assessing Treatment of Delirium

To delineate and assess the effectiveness of mifepristone in ameliorating the symptoms of delirium, formal psychiatric assessment and a battery of neuro-psychological tests and assessments are administered to all patients. The patients' performance on a standardized test instrument appropriate to the form of delirium under study will be determined. These tests and diagnostic assessments take place at baseline (patient's entry into treatment) and periodically throughout treatment.

Example 2

Measure Cortisol Levels

To measure cortisol levels of the patients of Example 1, afternoon Cortisol Test measurements are taken and used as the baseline cortisol measure. Cortisol levels are taken at Day 0, at two weeks after receiving the medication (Day 14), and each visit for up to six months and periodically thereafter.

The "Double Antibody Cortisol Kit" (Diagnostic Products Corporation, Los Angeles, Calif.) is used to measure blood cortisol levels. This test is a competitive radioimmunoassay in which $^{125}$I-labeled cortisol competes with cortisol from an clinical sample for antibody sites, and is performed essentially according to manufacturer's instructions using reagents supplied by manufacturer. Briefly, blood is collected by venipuncture and serum separated from the cells. The samples are stored at 2 to 8° C. for up to seven days, or up to two month frozen at −20° C. Before the assay, samples are allowed to come up to room temperature (15-28° C.) by gentle swirling or inversion. Sixteen tubes in duplicate at 25 microliters of serum per tube are prepared. Cortisol concentrations is calculated from the prepared calibration tubes. Net counts equals the average CPM minus the average non-specific CPM. Cortisol concentrations for the unknowns is estimated by interpolation from the calibration curve (Dudley, et al. (1985) Clin. Chem. 31:1264-1271).

It is understood that the examples and embodiments described herein are for illustrative purposes only and that various modifications or changes in light thereof will be suggested to persons skilled in the art and are to be included within the spirit and purview of this application and scope of the claims.

What is claimed is:

1. A method of ameliorating the symptoms of delirium in a patient in need thereof by administration of an amount of a specific non-steroidal glucocorticoid receptor antagonist effective to ameliorate the symptoms of delirium, with the proviso that the patient be not otherwise in need of treatment with a specific glucocorticoid receptor antagonist.

2. The method of claim 1, wherein the specific non-steroidal glucocorticoid receptor antagonist is administered in a daily amount of between about 0.5 to about 20 mg per kilogram of body weight per day.

3. The method of claim 2, wherein the specific non-steroidal glucocorticoid receptor antagonist is administered in a daily amount of between about 1 to about 10 mg per kilogram of body weight per day.

4. The method of claim 3, wherein the specific non-steroidal glucocorticoid receptor antagonist is administered in a daily amount of between about 1 to about 4 mg per kilogram of body weight per day.

5. The method of claim 1, wherein the administration is once per day.

6. The method of claim 1, wherein the mode of administration is oral.

7. The method of claim 1, wherein the mode of administration is by a transdermal application, by a nebulized suspension, or by an aerosol spray.

* * * * *